(12) United States Patent
Harttig

(10) Patent No.: US 11,027,869 B2
(45) Date of Patent: Jun. 8, 2021

(54) METHOD FOR SEPARATE STERILIZATION AND ASEPTIC ASSEMBLY

(71) Applicant: ROCHE DIABETES CARE, INC., Indianapolis, IN (US)

(72) Inventor: Herbert Harttig, Neustadt (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 192 days.

(21) Appl. No.: 15/982,629

(22) Filed: May 17, 2018

(65) Prior Publication Data

US 2018/0265237 A1 Sep. 20, 2018

Related U.S. Application Data

(63) Continuation of application No. PCT/EP2016/078082, filed on Nov. 17, 2016.

(30) Foreign Application Priority Data

Nov. 19, 2015 (EP) ..................... 15195346

(51) Int. Cl.
*B65B 55/02* (2006.01)
*A61B 5/145* (2006.01)
(Continued)

(52) U.S. Cl.
CPC .......... *B65B 55/02* (2013.01); *A61B 5/14532* (2013.01); *A61L 2/087* (2013.01);
(Continued)

(58) Field of Classification Search
CPC .......... A61B 2562/24; A61B 2562/242; A61B 5/14532; A61L 2/04; A61L 2/087;
(Continued)

(56) References Cited

U.S. PATENT DOCUMENTS 3,783,581 A * 1/1974 Pierce .................. B65B 55/027
53/426
4,019,512 A 4/1977 Tenczar
(Continued)

FOREIGN PATENT DOCUMENTS

CN 1078375 A 11/1993
CN 1337862 A 2/2002
(Continued)

OTHER PUBLICATIONS

International Search Report and Written Opinion of the International Searching Authority, PCT/EP2016/078082, dated Mar. 17, 2017, 9 pages.
(Continued)

*Primary Examiner* — Hemant Desai
*Assistant Examiner* — Jacob A Smith
(74) *Attorney, Agent, or Firm* — Bose McKinney & Evans LLP

(57) ABSTRACT

Disclosed is an inventive method for an aseptic assembly of a multi-component medical device. In this method a first component of the medical device is provided in a first container and a second component of the medical device is provided in a second container. Each of the first and second separated containers have a rupturable portion. The first component in the first container is sterilized using a first sterilization technique and the second component in the second container is sterilized using a second sterilization technique. The first and second containers are joined while arranging the rupturable portions in an overlapping configuration which is aseptically sealed against the surroundings. Finally, one of the components is transferred through the rupturable portions and the components are aseptically assembled to form the medical device as a sterile package.

22 Claims, 3 Drawing Sheets

(51) Int. Cl.
*A61L 2/08* (2006.01)
*A61L 2/20* (2006.01)
*A61M 5/00* (2006.01)
*A61M 5/14* (2006.01)
*A61L 2/04* (2006.01)

(52) U.S. Cl.
CPC .............. *A61L 2/206* (2013.01); *A61M 5/001* (2013.01); *A61M 5/1413* (2013.01); *A61B 2562/242* (2013.01); *A61L 2/04* (2013.01); *A61L 2202/181* (2013.01); *A61L 2202/23* (2013.01); *A61L 2202/24* (2013.01)

(58) Field of Classification Search
CPC ............... A61L 2/206; A61L 2202/181; A61L 2202/23; A61L 2202/24; A61M 5/00; A61M 5/1413; B65B 55/02; B65B 55/025; B65B 55/027; B65B 55/04; B65B 55/12
USPC ........... 53/425, 426, 428, 432; 422/3, 22, 23
See application file for complete search history.

(56) References Cited

U.S. PATENT DOCUMENTS

| | | | | |
|---|---|---|---|---|
| 4,030,494 | A * | 6/1977 | Tenczar | A61M 39/14 604/411 |
| 4,161,949 | A | 7/1979 | Thanawalla | |
| 4,494,363 | A * | 1/1985 | Rica | B65B 55/022 53/426 |
| 5,492,147 | A | 2/1996 | Challender et al. | |
| 6,224,568 | B1 * | 5/2001 | Morimoto | A61J 1/2089 604/89 |
| 8,133,204 | B1 * | 3/2012 | Kriesel | A61M 5/148 604/132 |
| 2009/0061751 | A1 * | 3/2009 | Polsky | B08B 15/026 454/57 |
| 2010/0056995 | A1 * | 3/2010 | Kriesel | A61M 39/18 604/83 |
| 2010/0056997 | A1 * | 3/2010 | Kriesel | A61M 5/16881 604/85 |
| 2010/0056998 | A1 * | 3/2010 | Kriesel | A61M 39/18 604/85 |
| 2012/0087829 | A1 * | 4/2012 | Lindblad | B65B 31/02 422/28 |
| 2012/0305427 | A1 * | 12/2012 | Felder | A61B 50/30 206/438 |
| 2013/0142694 | A1 * | 6/2013 | Krohmann | A61L 2/14 422/29 |
| 2013/0150691 | A1 * | 6/2013 | Pace | A61B 5/1451 600/347 |
| 2013/0296803 | A1 * | 11/2013 | Kriesel | A61M 5/148 604/246 |
| 2014/0183094 | A1 * | 7/2014 | Imai | A61J 1/00 206/528 |
| 2014/0348703 | A1 | 11/2014 | Thomas et al. | |
| 2015/0129437 | A1 * | 5/2015 | Clamp | A45C 11/005 206/5.1 |
| 2015/0183541 | A1 * | 7/2015 | Deutschle | B65B 51/10 206/439 |
| 2016/0051329 | A1 * | 2/2016 | Verschuur | A61B 50/30 422/310 |

FOREIGN PATENT DOCUMENTS

| | | |
|---|---|---|
| CN | 1352570 A | 6/2002 |
| CN | 1750970 A | 3/2006 |
| CN | 101588837 A | 11/2009 |
| CN | 102482023 A | 5/2012 |
| EP | 1 972 275 A1 | 9/2008 |
| EP | 2 713 879 B1 | 7/2017 |
| WO | WO 00/62820 A2 | 10/2000 |
| WO | WO 2006/121661 A2 | 11/2006 |
| WO | WO 2008/070220 A1 | 6/2008 |
| WO | WO-2008070220 A1 * | 6/2008 ............ A61M 39/18 |
| WO | WO 2012/114105 A1 | 8/2012 |
| WO | WO 2013/090215 A2 | 6/2013 |

OTHER PUBLICATIONS

International Preliminary Report on Patentability, PCT/EP2016/078082, dated May 8, 2018, 13 pages.

* cited by examiner

METHOD FOR SEPARATE STERILIZATION AND ASEPTIC ASSEMBLY

RELATED APPLICATIONS

This application is a continuation of PCT/EP2016/078082, filed Nov. 17, 2016, which claims priority to EP 15 195 346.0, filed Nov. 19, 2015, the entire disclosures of both of which are hereby incorporated herein by reference.

BACKGROUND

This disclosure concerns a method for an aseptic assembly of a multi-component medical device, in particular a skin-mountable sensor device for example as a system for continuous glucose monitoring. This disclosure further relates to an aseptic kit for providing such a multi-component medical device.

U.S. Publication No. 2014/0348703 A1 notes that it is important for devices that are to be implanted in the body or positioned below a skin surface of a user, to be sterile upon insertion. In this context, said document discloses methods and systems for the sterilization of medical devices, including devices for the continuous or automatic monitoring of analytes, such as glucose, in bodily fluid. There is provided assembling an analyte sensor with an analyte sensor insertion device, packing the assembled analyte sensor and sensor insertion device in a container which may optionally include a substantially airtight seal, and irradiating the packaged assembled analyte sensor and sensor insertion device at a dose effective to sterilize the package. However, this sterilization approach leads into a dilemma when electronic units, such as signal amplifiers, and adherent coatings are impaired by ionizing radiation.

The present applicants have observed that it is difficult to shield sensitive units from ionizing radiation. Disadvantageously in radiation screening is also the necessary shielding material mass, which increases costs of manufacture and volume of packaging. On the other hand, additional components such as enzyme-containing sensor elements may become deactivated by reactive sterilization gases. A problem associated therewith lies in the fact that the commonly used ethylene dioxide gas dissolves in usual packaging materials, thus requiring overpackaging for the gas-sensitive system parts.

SUMMARY

On this basis, this disclosure further improves the known methods and devices and provides easy-to-use and reliable arrangements for sterilized multi-component medical devices.

This disclosure is based on the idea of providing a sterile port in an aseptic package of separately sterilized components. Accordingly it is proposed according to this disclosure that the method mentioned at the outset comprises the following steps:
  providing a first component of the medical device in a first container and a second component of the medical device in a second container, wherein each of the separated containers comprises a rupturable portion,
  sterilizing the first component in the first container using a first sterilization technique and sterilizing the second component in the second container using a second sterilization technique,
  joining the first and second container while arranging the rupturable portions in an overlapping configuration which is aseptically sealed against the surroundings,
  transferring one of the components through the rupturable portions and aseptically assembling the components to form the medical device as a sterile package.

In this way, this disclosure provides a simple method to separately sterilize sensitive system components such that they can be assembled aseptically. The utility of a two- or multi-piece separated but combinable container arrangement enables to apply respective sterilization techniques which are not impairing the operativeness and reliability of the sterilized components. Still other advantages may exist, where in case of different shelf-life the sterilization processes may be adjusted accordingly. Advantageously, the provisions according to this disclosure result in a reduction of costs as the sterilization volume for radiation sterilization is reduced, not further shield need to be included and the assembly within the container arrangement can be carried out side of a clean room potentially even by a user.

According to one embodiment, the first and second sterilization techniques are different from each other and are selected from the group consisting of gas sterilization (preferably using ethylene oxide gas), irradiation sterilization (preferably using an electron beam) and thermal sterilization. This allows also that the packaging can be adapted to the respective sterilization technique.

Advantageously, one of the containers has a gas-permeable and aseptically sealing membrane, wherein a sterilization gas is introduced and released through the membrane such that no potentially harmful gas remains after achieving a desired sterility level. This may be further facilitated by use of a pressure alternating procedure.

A plurality of first or second containers including respective components can be arranged in a sterile-tight outer covering before the sterilizing step, thereby reducing operating expense and allowing for sterile intermediary transport.

In this context, it is also advantageous when the first and second container are joined in a sterile environment.

According to one implementation, at least one of the first and second containers has an adhesive portion, and the containers are adhered to each other using the adhesive portion.

For further improvement of sterile assembly it is advantageous when an aseptic seal is formed around the rupturable portions by bonding together sealing portions of the first and second container.

Another mounting improvement provides that the step of transferring one of the components includes rupturing both of the rupturable portions.

In this connection, it is also advantageous when the component to be transferred is used to rupture the rupturable portions.

Advantageously, at least one of the first and second components may be manipulated by handling means or handle provided within the containers.

A particular embodiment further comprises providing one of the first and second containers as a flexible bag or bellow and compressing the flexible bag or bellow to move the component included therein.

Another handling improvement may be achieved when at least one of the first and second containers has a flexible wall, and when at least one of the first and second components is manipulated through the flexible wall to form the medical device.

From the manufacturing point of view it is advantageous when forming at least a part of the containers from a plastic material preferably by means of injection molding or blow molding or deep drawing.

For further improvement of the usability it is advantageous to form at least one of the rupturable portions from a foil material, preferably a metal foil.

Another aspect of this disclosure concerns an aseptic kit for a multi-component medical device, in particular a skin-mountable sensor device, comprising a first component of the medical device in a first container and a second component of the medical device in a second container, wherein the components are maintained sterile within the containers, characterized in that each of the containers comprises a rupturable portion, and that the first and second container are connected to each other such that the rupturable portions are arranged in an overlapping configuration which is aseptically sealed against the surroundings.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
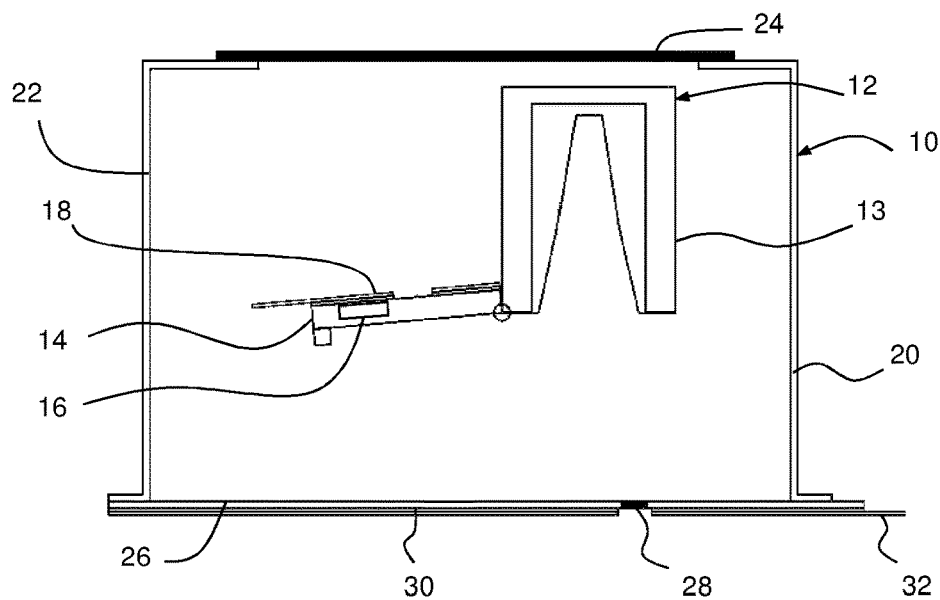
FIG. 1 is a section view of a first container including an applicator unit of a continuous blood glucose measuring device.

FIG. 1 shows a first container 10 including a first component 12 of a multi-component medical device. In this embodiment, the first component 12 includes an applicator unit 13 which is combined with a patch 14 containing electronic components 16 and an adhesive pad 18. The first container 10 has a rigid wall 20, a transparent flexible wall 22, a gas-permeable membrane 24 and a cover lid 26 which is provided with a first rupturable portion 28 and which is coated with an adhesive layer 30 covered by a liner 32.

Figure 2:
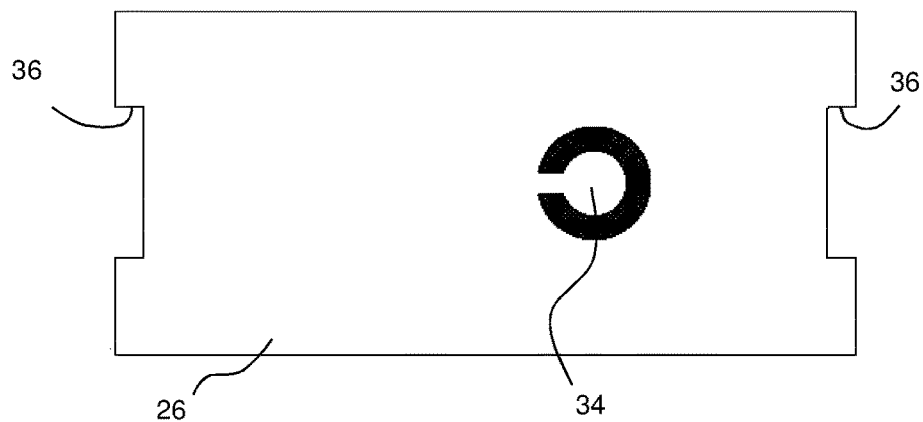
FIG. 2 is a top view of a cover lid of the first container having a rupturable portion.

As apparent from FIG. 2, the first rupturable portion 28 is formed as a circular insert preferably from aluminum foil and is reinforced by a central flap 34 providing a bendable connecting link 4 to the lid 26. Advantageously, the lid 26 is configured with lateral cutaways 36 as positioning aids to be explained further below.

In the state illustrated in FIG. 1, the first component 12 can be sterilized using a gas sterilization technique without impairing the adhesiveness of the pad 18 and without damaging the electronics 16. In a certain embodiment, ethylene dioxide as sterilizing gas is introduced and released through the gas-permeable membrane 24 by use of a pressure alternating procedure. For further efficiency improvement of this sterilization procedure, a plurality of first containers 10 comprising respective first components 12 may be arranged in a sterile-tight outer covering (not shown).

Figure 3:
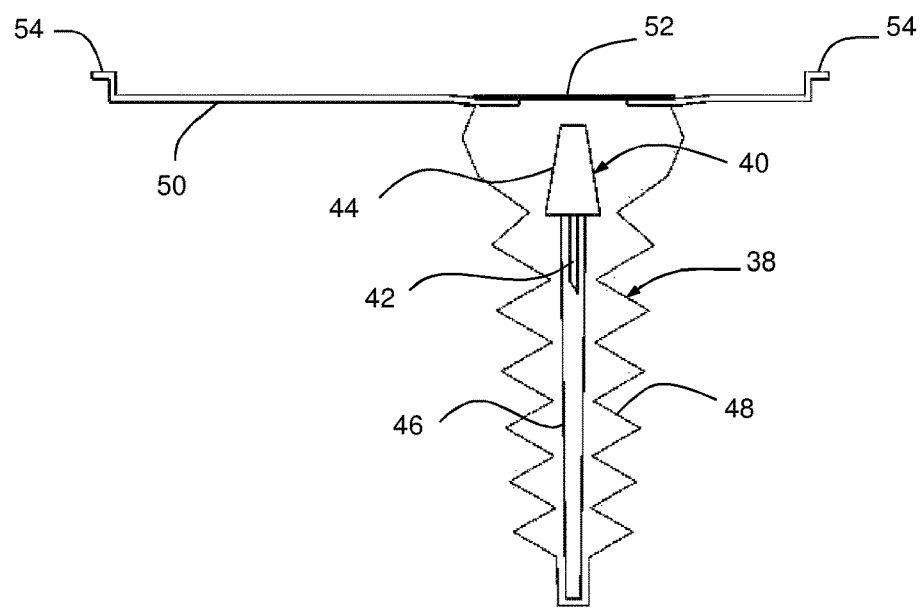
FIG. 3 is a section view of a second container including a skin-insertable sensor unit of the measuring device.

Turning now to FIG. 3, a second container 38 holds a second component 40 of the multi-component medical device. In one embodiment, the second component 40 includes an inserter unit 42 for a skin-implantable sensor which is combined with a carriage 44 designed for a connection to applicator 13 and with a transport sleeve 46 provided as a handling aid.

The second container 38 comprises a bellow 48 and a connector lid 50 which is provided with a second rupturable portion 52 and lateral joining portions 54. The rupturable portion 52 consists of aluminum foil and covers an outlet of the bellow 48. If necessary, a drying agent or sorbent may be included in the second container 38.

In the state illustrated in FIG. 3, the second component 40 can be sterilized using an irradiation sterilization technique. All elements in the second container 38 are radiation-proof and reveal low outgassing. In one embodiment, electron beam irradiation is applied. The electron beam may be configured to irradiate the second container 38 at a dosage of approximately 25 kGy which results in an adequate sterility assurance level. Preferably, a plurality of second containers 38 is packed densely in a sterile-tight outer covering during the sterilization process. In this case, any shielding of the scanning electron beam should be avoided.

After separate sterilization of the first and second components 12, 40, the first and second containers 10 and 38 may be joined in order to allow the assembly of the medical device. This should take place in a sterile environment, e.g. in a flow-box provided with a sterile filter and UV-lamp, wherein the containers 10, 38 are withdrawn from the respective outer covering and are adhered to each other using the adhesive layer 30 after removing the liner 32.

Figure 4:
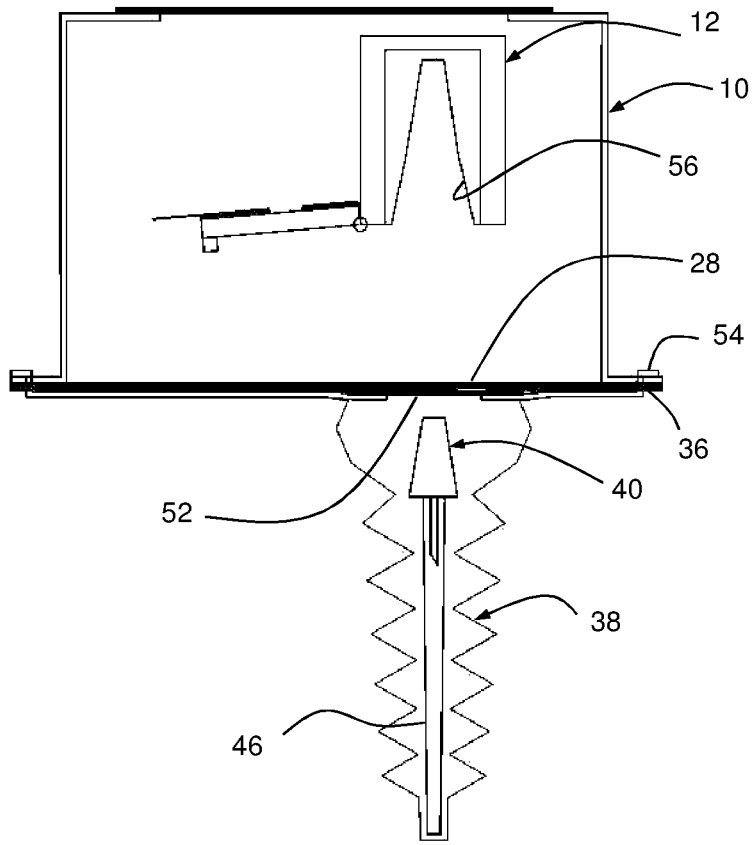
FIG. 4 is a section view of the joined first and second container.

In the joined configuration shown in FIG. 4, the joining portions 54 of the connector lid 50 engage the lateral cutaways 36 of the cover lid 26 in a form-locking manner, such that a defined mutual orientation is achieved in which the rupturable portions 28, 52 overlap each other. Due to the planar adhesive connection via the adhesive layer 30, an aseptic seal around the rupturable portions 28, 52 is formed which is sterile-tight against the surroundings or environment of the joined container configuration. In this way, as sterile kit is formed which allows to separately store the components 12, 40 in their respective containers 10, 38 and to assemble the complete system only at the time of use. In the case of putting together the components by the user himself, the handling aid 46 and guiding means 56 are provided to allow the correct accomplishment of the necessary steps while considerably reducing the possibility of errors.

As the case may be, the final aseptic assembly is carried out as described hereinafter in connection with FIGS. 5 to 7.

Figure 5:
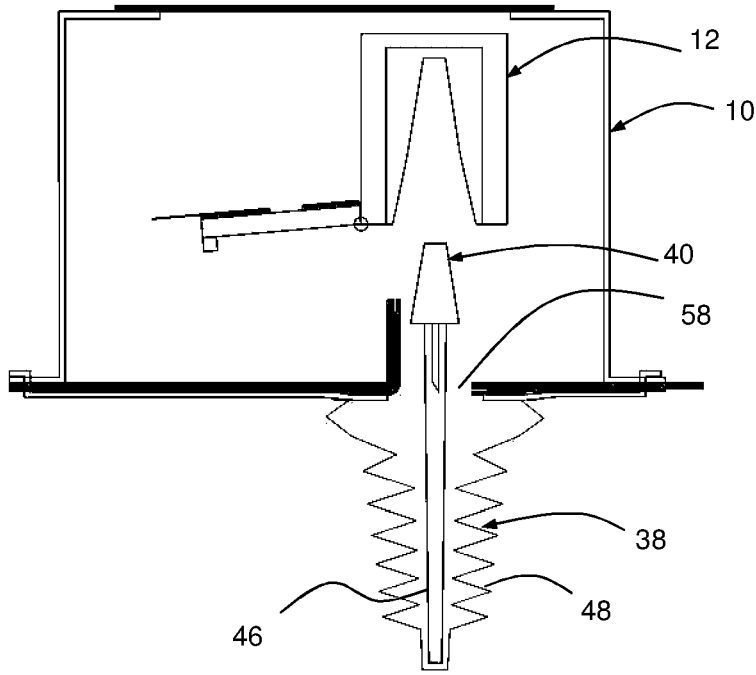
FIGS. 5-7 illustrate the assembling of the measuring device under sterile conditions within the joined containers.

According to FIG. 5, the second component 40 is transferred through the rupturable portions 28, 52 into the first container 10. For this purpose, the free end of the handling aid 46 has to be grasped through the bellow 48 to allow for moving the second component 40 in direction to the first component 12. Thereby, the carriage 44 is used to rupture or tear-open both of the rupturable portions 28, 52 and to establish an open port 58 without compromising the sterility within the containers 10, 38.

Potentially present germs which may have been deposited onto one of the lids 26, 50 after the sterilization steps will be immobilized by the adhesive layer 30. Germs which were able to reach the airspace inside one of the containers when the rupturable portions 28, 52 are broken, can settle down only onto the transport sleeve 46 or other uncritical surfaces. The probability of a viable germ to settle down onto a body contacting surface during assembly is extremely low due to additional protection by liners and/or protective covers.

Figure 6:
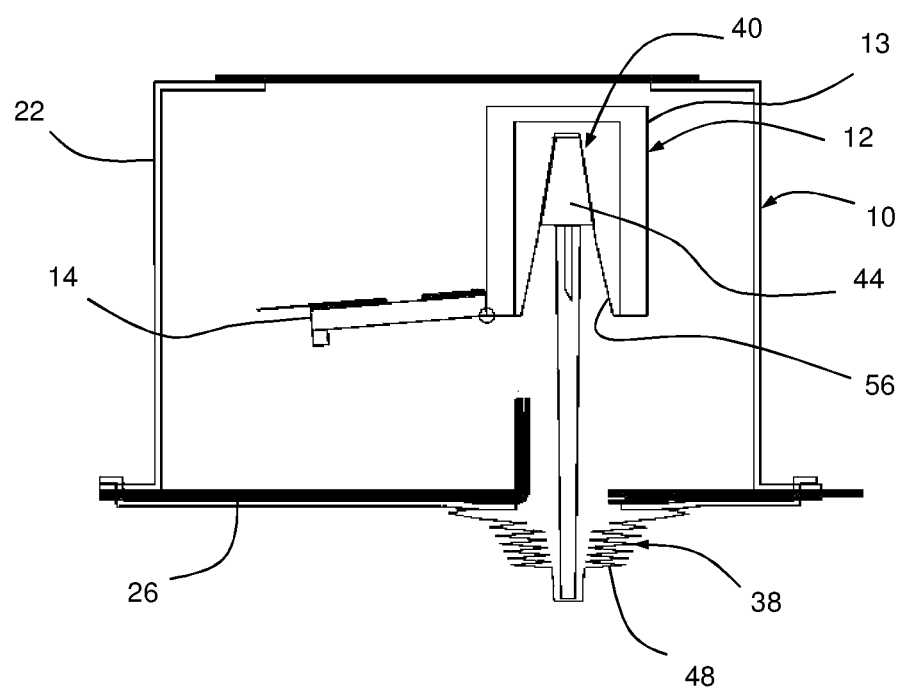

Now, once introduced into the guiding means 56 of the first component 12, the carriage 44 links with the applicator 13, as illustrated in FIG. 6. This allows the withdrawing of the transport sleeve 46, which remains in the bellow 48. Subsequently the patch 14 may be swiveled against the applicator 13, where the flexible wall 22 allows the necessary manipulation. Then, the assembly is completed, resulting in a sterile arrangement of the combined first and second components 12, 40.

Figure 7:
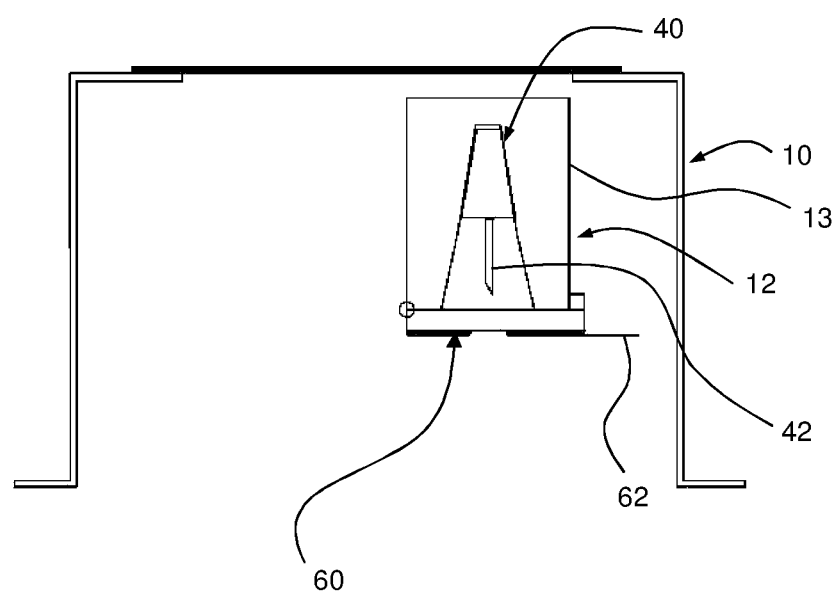

Turning now to FIG. 7, the assembled medical device 60 consisting of first and second components 12, 40 is shown ready to use, when the cover lid 26 has been removed from the first container 10. The user removes the liner 62 from the adhesive pad 18 and adheres the device 60 to the skin of a body part. Then, the applicator 13 is triggered and the inserter unit 42 implants the sensor in the skin. After separating the applicator 13, the skin-mounted pad 14 is ready for docking a reusable processor unit, which as such is not sterilized.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for an aseptic assembly of a multi-component medical device, comprising:
   a) providing a first component of the medical device in a first container having a first rupturable portion;
   b) providing a second component of the medical device in a second container having a second rupturable portion;
   c) sterilizing the first component in the first container using a first sterilization technique and sterilizing the second component in the second container using a second sterilization technique, wherein the first and second sterilization techniques are different and are selected from the group consisting of gas sterilization, irradiation sterilization, and thermal sterilization;
   d) joining the first and second containers to form a sterile kit wherein the first and second rupturable portions are arranged in an overlapping configuration which is aseptically sealed against the surroundings;
   e) transferring one of the components through the first and second rupturable portions and aseptically assembling the components to form the medical device as a sterile package; and wherein step e is performed within an interior space enclosed by the first and second containers and wherein the method further comprises removing the medical device assembled during step e from the first and second containers before using the medical device.

2. The method according to claim 1, wherein one of the containers has a gas-permeable and aseptically sealed membrane, and wherein a sterilization gas is introduced and released through the membrane.

3. The method according to claim 2, wherein the sterilization gas is introduced and released through the membrane by a pressure alternating procedure.

4. The method according to claim 1, wherein one of the first and second sterilization techniques is gas sterilization with ethylene oxide gas.

5. The method of claim 4, wherein one of the containers has a gas-permeable and aseptically sealing membrane, and wherein the ethylene oxide gas is introduced and released through the membrane.

6. The method according to claim 1, wherein one of the first and second sterilization techniques uses an electron beam.

7. The method according to claim 1, further comprising arranging a plurality of first or second containers including respective components in a sterile-tight outer covering before the sterilizing step.

8. The method according to claim 1, wherein step d is performed in a sterile environment and step e is performed after removing the sterile kit from the sterile environment.

9. The method according to claim 1, wherein at least one of the first and second containers has an adhesive portion, and wherein the containers are adhered to each other using the adhesive portion.

10. The method according to claim 1, further comprising forming an aseptic seal around the rupturable portions by bonding together sealing portions of the first and second containers.

11. The method according to claim 1, wherein the step of transferring one of the components includes rupturing both the first and second rupturable portions.

12. The method according to claim 1, wherein the component to be transferred is used to rupture the first and second rupturable portions.

13. The method according to claim 1, further comprising manipulating at least one of the first and second components by using a handling aid provided within the containers.

14. The method according to claim 1, further comprising providing one of the first and second containers as a flexible bag or bellow and compressing the flexible bag or bellow to move the component included therein.

15. The method according to claim 1, wherein at least one of the first and second containers has a flexible wall, and wherein at least one of the first and second components is manipulated through the flexible wall to form the medical device.

16. The method according to claim 1, further comprising forming at least a part of the containers from a plastic material.

17. The method according to claim 16, wherein the forming of the at least a part of the containers comprises injection molding, blow molding or deep drawing.

18. The method according to claim 1, further comprising forming at least one of the first and second rupturable portions from a thin flexible sheet of material.

19. The method according to claim 18, wherein the thin flexible sheet of material is a metal foil.

20. The method according to claim 1, wherein the multi-component medical device is a skin mountable sensor device.

21. An aseptic kit for a multi-component medical device, comprising: a first component of the medical device in a first container having a first rupturable portion and a second component of the medical device in a second container having a second rupturable portion, wherein the first component is maintained sterile by a first sterilization technique and the second component is maintained sterile by a second sterilization technique different than the first sterilization technique, the first and second sterilization techniques being selected from the group consisting of gas sterilization, irradiation sterilization and thermal sterilization;

wherein the first and second containers are connected to each other such that the first and second rupturable portions are arranged in an overlapping configuration and wherein the first and second containers are bonded to each other to form an aseptic seal around the first and second rupturable portions; and wherein one of the first and second components is configured to be transferred through the first and second rupturable portions to assemble the medical device; and wherein the first rupturable portion is disposed on a lid attached to the first container, the lid being configured such that detachment of the lid from the first container allows removal of the medical device from the first and second containers before use of the medical device.

22. The aseptic kit of claim 21, wherein the multi-component medical device is a skin mountable sensor device.

\* \* \* \* \*